United States Patent [19]

Charpentier

[11] Patent Number: 4,757,259
[45] Date of Patent: Jul. 12, 1988

[54] METHOD FOR MEASURING THE THICKNESS AND TEMPERATURE OF A MOVING METAL SHEET BY MEANS OF EDDY CURRENTS

[75] Inventor: Jacques Charpentier, Moirans, France

[73] Assignee: Cegedur Societe de Transformation de l'Aluminium Pechiney, Paris, France

[21] Appl. No.: 927,089

[22] Filed: Nov. 5, 1986

[30] Foreign Application Priority Data

Nov. 6, 1985 [FR] France ................................ 85 16791

[51] Int. Cl.$^4$ ...................... G01B 7/10; G01N 27/72; G01R 33/02
[52] U.S. Cl. .................................... 324/227; 324/229; 324/232
[58] Field of Search ............... 324/202, 203, 204, 206, 324/224–233, 239–243

[56] References Cited

U.S. PATENT DOCUMENTS

| | | | |
|---|---|---|---|
| 2,989,691 | 6/1961 | Cook | 324/224 X |
| 3,568,050 | 3/1971 | Dill | 324/203 X |
| 3,651,398 | 3/1972 | Urmenyl | 324/229 X |
| 3,725,778 | 4/1973 | Leonard et al. | 324/227 |
| 3,848,466 | 11/1974 | Dial et al. | 324/224 X |
| 3,936,734 | 2/1976 | Brandli et al. | 324/203 X |
| 3,950,993 | 4/1976 | Sidor | 324/224 X |
| 4,534,405 | 8/1985 | Hulek et al. | 324/229 X |

FOREIGN PATENT DOCUMENTS 1385198  2/1975  United Kingdom ................ 324/203

Primary Examiner—Reinhard J. Eisenzopf
Assistant Examiner—Warren S. Edmonds
Attorney, Agent, or Firm—Dennison, Meserole, Pollack & Scheiner

[57] ABSTRACT

A non-contacting, eddy current, measuring method for determining the thickness and temperature of a moving metal sheet as in a metal rolling operation. Two separate magnetic fields are generated by applying two voltages of differing frequencies to a primary winding on one side of the sheet to induce two voltages in an opposed secondary winding on the other side of the sheet. The generated voltages are used to determine the calibration constants required to calculate the thickness and temperature of the moving sheet.

10 Claims, 1 Drawing Sheet

METHOD FOR MEASURING THE THICKNESS AND TEMPERATURE OF A MOVING METAL SHEET BY MEANS OF EDDY CURRENTS

BACKGROUND OF THE INVENTION

The invention relates to a process for the non-contacting measurement while moving of the thickness and temperature of thin metal sheets by means of Foucault or eddy currents.

The man skilled in the art is aware of the advantages in being able to measure the thickness of metal sheets issuing from a rolling mill, while the metal sheets are moving along, so as to be able to regulate the rolling parameters within limits which make it possible either to maintain a constant thickness of metal sheet or to vary the thickness of the metal sheet as desired, according to user needs.

That problem arises in particular when rolling thin sheets in particular of aluminium in a range of thicknesses of between 8 and 2000 μm.

Due to the increase in rolling speeds, in order to make such measurements, recourse is preferably had to apparatuses in which the measuring element is not in contact with the sheet in order not to leave any mark nor to cause problems in the measuring operation by virtue of the measuring element suffering from progressive wear.

That is the case for example with apparatuses using eddy currents or radiation in which the measuring element operates at a certain distance from the sheet.

Among such arrangements, that which uses eddy currents has the advantage of being simple, low in cost and high in reliability.

The principle thereof is as follows:

A primary winding is supplied with an alternating signal by an oscillator; that winding therefore generates an alternating magnetic field which induces a current in a winding which is referred to as a secondary winding, using the same principle as a transformer, and develops an electrical voltage therein.

When a metal sheet is placed between the windings, the magnetic field generated by the first winding induces a current in the sheet. That current in turn generates a field which opposes that which gave rise thereto. The consequence thereof is to cause the voltage in the second winding to fall. If a thicker sheet is set in position between the windings, the induced currents are higher and the voltage drops even more in the secondary winding. It is thus possible to measure the thickness of the aluminium sheet in the course of rolling in a contact-less manner by measuring the voltage developed in the secondary winding.

However that type of measuring operation suffers from a major disadvantage: the induced current is proportional to the product $\sigma \times e$ (a relationship established by Forster) in which $\sigma$ is the conductivity of the sheet and $e$ is its thickness. Now, $\sigma$ depends not only on the composition of the metal and its structure but also its temperature. If in the course of rolling a strip, it is possible to ensure that the product is homogenous, that is not true in regard to temperature.

In fact, it is known that, in the course of an operation of rolling aluminium sheets, the temperature parameter may vary by several tens of degrees. That means that such a process, when applied to measurement in respect of thickness at the discharge of a rolling mill will give rise to erroneous measurements by virtue of the interference of the effects of temperature.

SUMMARY OF THE INVENTION

It is for that reason that the applicants researched into and found the process which makes it possible simultaneously to measure thickness and conductivity and therefore to obtain correct values in respect of thickness, irrespective of the temperature and/or to measure in a non-contacting manner the temperature of the sheet, irrespective of its thickness, if its conductivity is assumed to be constant.

The process for non-contacting measurement while moving by means of eddy currents of the thickness ($e$) in micrometers and the temperature ($\theta$) in degrees C. of a thin metal sheet is characterised by generating on the same side of the sheet two separate magnetic fields by applying to at most two primary windings (A1) and (A2) a voltage V1 of a frequency N1 and a voltage V2 of a frequency N2 so as to develop respectively the induced voltages V'1 and V'2 in at most two secondary windings (B1) and (B2) placed on the other side of the sheet and respectively facing (A1) and (A2), determining a voltage U1 in volts in the electrical circuit using V1 and V'1 and a voltage U2 in the circuit V2 and V'2, calculating the values of $e$ and $\theta$ in the following manner:

first establishing:

on the one hand the relationship $U = K/e + C$ which is obtained by measuring the voltages $U^{e}1$ generated by a field of frequency N1 when it passes through sheets of different thicknesses but at a constant temperature and likewise the voltages $U^{e}2$ for a frequency N2, and deducing the values of the constants C1 and C2 respectively corresponding to the values of C for the frequencies N1 and N2, it being known that the 0 of the voltage measuring apparatus has been regulated to a reference thickness $e_0$ and a temperature $\theta_0$, on the other hand, the relationship $U = b + a\theta$ which is obtained by measuring the voltages $U^{\theta}1$ generated by a field of frequency N1 when it passes through sheets at different temperatures but of constant thickness and likewise for the voltages $U^{\theta}2$, the zero of the voltage measuring apparatus also being regulated for $e_0$ and $\theta_0$ and deducing the values of the constants a1, a2 and b1, b2 whose indices 1 and 2 correspond to the frequencies N1 and N2, using the values of said constants to determine the values of other constants A1, A2, B1 and B2 from the following equations:

$$A_1 = (b_1 - C_1)e_0, \quad A_2 = (b_2 - C_2)e_0$$
$$B_1 = a_1 e_0, \quad B_2 = a_2 e_0$$

introducing the values of the constants A1, B1, C1, A2, B2, C2 and the values of the voltages U1 and U2 observed on the sheets to be measured into the following formulae:

$$e = [A_1 B_2 - A_2 B_1]/[(U_1 - C_1)B_2 - (U_2 - C_2)B_1] \text{ and}$$

$$\theta = [A_2(U_1 - C_1) - A_1(U_2 - C_2)]/[B_1(U_2 - C_2) - B_2(U_1 - C_1)]$$

DESCRIPTION OF THE PREFERRED EMBODIMENTS

Figure 1:
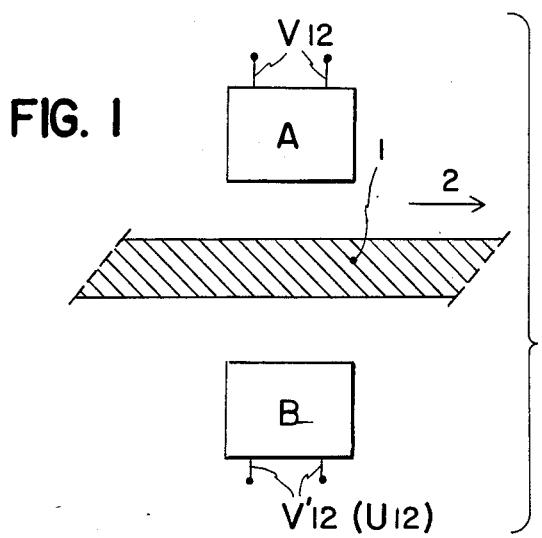
FIG. 1 is a simplified schematic showing a single primary winding A fed by two voltages V1, V2 for inducing voltages V'1 and V'2 in a single secondary winding B oppositely spaced across the moving metal sheet.

Thus the invention involves generating on the same side of the sheet two separate magnetic fields of frequencies N1 and N2 which are preferably between $1.10^2$ and $1.10^5$ Hertz. The frequency used depends on the thickness of the sheet to be measured and decreases in proportion to increasing thickness. The range used here is perfectly suitable for sheets of a thickness of between 8 and 2000 $\mu$m and preferably between 8 and 100 $\mu$m. Those fields are produced by means of at most two primary coils or windings (A1) and (A2) which are generally each formed by an insulated electrical wire which is wound around an insulating core and whose ends form the terminals of the winding.

The expression "at most two windings" should be interpreted to mean that the use of a higher number of windings, while being possible, would only complicate the process without giving substantial advantages.

The different constructions involved in that expression should now be described.

It is first necessary to look at the situation using a single primary winding. The winding is then connected to two low-voltage alternating current sources V1 and V2 which are respectively operating at frequencies N1 and N2. That winding whose core is generally perpendicular to the sheet is so positioned that the lower face of its protective casing cannot come into contact with the top of the sheet, that generally corresponding to a distance of between 10 mm and several centimeters.

Disposed facing that winding and on the other side of the sheet, in approximately symmetrical relationship, is a secondary winding (B) of the same constitution as the winding (A) and in which the ends of the wire, by virtue of induction phenomena, develop a voltage V'1 at a frequency N1 and a voltage V'2 at a frequency N2.

The voltages U1 and U2 whose indices respectively correspond to the frequencies N1 and N2 and which are determined for the purposes of incorporation thereof into the formulae for calculating thickness and temperature can be obtained in two different ways:

either using the values of the voltages V'1 and V'2 after amplification, which reference U1 and U2, or detecting the phase displacement on the one hand between V1 and V'1 and on the other hand between V2 and V'2, and transforming the phase displacement values by electronic means into voltage values which are also amplified and which give U1 and U2.

However, a problem arises by virtue of the fact that the currents of a frequency N1 and N2 are superimposed.

Two solutions can be used: either by applying the voltages V1 and V2 successively and synchronously measuring the voltages V'1 and V'2 or the phase displacements V1V'1 and V2V'2, or by simultaneously applying the voltages V1 and V2 and passing the induced voltage V'12 into frequency filters so as to be able to separate the components relating to each frequency and measure either the voltages V'1 and V'2 or the phase displacements V1V'1 and V2V'2. It will be apparent that in the latter case, the phase references are taken separately on each of the primary voltages before simultaneous application thereof to the primary windings so as not to have to separate them.

The expression "at most two windings" also covers the use of a primary winding (A1) which is supplied at a frequency N1 and a primary winding (A2) which is supplied at a frequency N2, the windings being disposed concentrically with each other and facing either a single winding B or two secondary windings (B1) and (B2) which are also disposed in concentric relationship.

In that case, the problems involved in superimposition of the currents also arise and it is necessary to use frequency filters, as before.

In that construction, the measurements in respect of U1 and U2 are made both on the basis of the measurements of V'1 and V'2 and the phase displacement measurements as between V1 and V'1 on the one hand and V2 and V'2 on the other hand.

Finally, the expression "at most two windings" also covers the use of two pairs of windings (A'1) and (B'1) and (A'2) and (B'2) which are disposed facing each other and in which (A'1) is supplied with a current at a frequency N1 and (A'2) is supplied with a current at a frequency N2. The measurements in respect of U1 and U2 are made in the same manner as with the concentric windings, but without filtering.

Those pairs are not excessively far from each other so as to provide a compact measuring assembly. They are aligned in any manner with respect to the direction of movement of the sheet but preferably in the direction of rolling.

The measurements in respect of the voltages U1 and U2 as described hereinbefore make it possible to determine at any time the thickness e in micrometers and the temperature $\theta$ in degrees C. of sheets which pass the measuring assembly, without the variations in e and $\theta$ interfering in the measurement of each of those parameters.

For that purpose, use is made of formulae which, besides the values of U1 and U2 which are a function respectively of each of the frequencies N1 and N2 and measured from the sheets to be tested, involve the values of constants A1, B1, C1 and A2, B2, C2 which are also relative to the frequencies N1 and N2 used. Those constants are themselves drawn from equations:

$$A = (b-C)e_0 \text{ and } B = ae_0$$

and relationships:

$U = K/e + C$ and $U = b + a\theta$ which have been established beforehand on the basis of a plurality of measurements in respect of $U^\theta 1$ and $U^\theta 2$ obtained on sheets of different thicknesses and at constant temperature and on the basis of a plurality of measurements of $U^\theta 1$ and $U^\theta 2$ on sheets of the same thickness but at different temperatures.

In both cases, the 0 of the voltage measuring apparatus is initially adjusted to a reference thickness $e_0$ and a temperature $\theta o$.

It will be apparent that the values of the constants can be put into the memory of a computer whose program then makes it possible to calculate the values of the measurements required, on the basis of the measurements in respect of U1 and U2 observed on any sheet.

The invention may be illustrated by means of the accompanying sheet of drawing which diagrammatically shows various possible ways of applying the process according to the invention. Shown therein is a sheet 1 which is displaced horizontally in a direction 2 in the air gap between one or more primary windings A and one or more secondary windings B.

The voltages V1 and V2 of respective frequencies N1 and N2 are applied to the winding or windings A and developed at the winding or windings B respectively are the induced voltages, being either separate voltages V'1 and V'2 or superposed voltages V'12, then being passed to frequency filters to separate them into V'1 and V'2. The voltages V'1 and V'2 or the phase displacements V1V'1 and V2V'2 are passed to amplifiers to give U1 and U2. The filtering and amplifying equipment is not shown herein.

Figure 2:
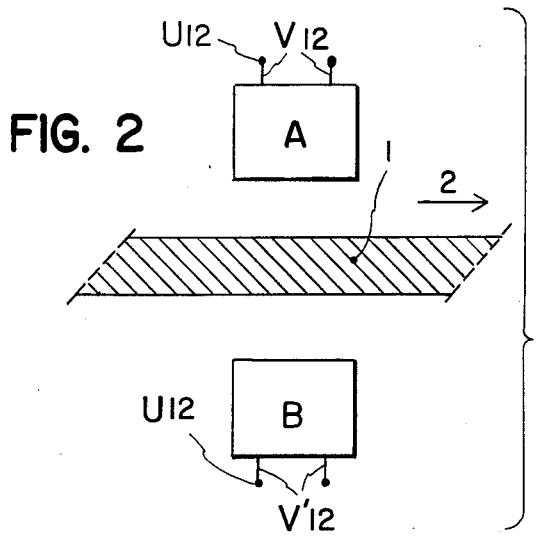
FIG. 2 is a simplified schematic similar to FIG. 1 showing single primary and secondary windings for generating phase displacement voltages V1V'1 and V2V'2.

FIGS. 1 and 2 relate to the use of a single primary winding A to which the voltages V1 and V2 are applied and a single secondary winding for developing the induced voltages V'1 and V'2. The voltages U1 and U2 correspond to V'1 and V'2 in FIG. 1 and to the phase displacements V1V'1 and V2V'2 in FIG. 2.

Figure 3:
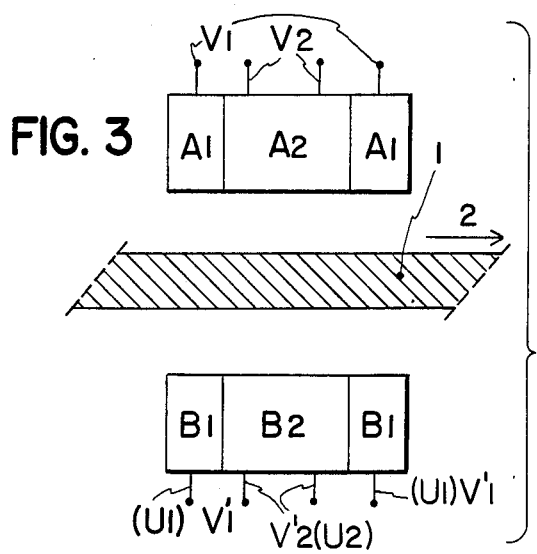
FIG. 3 is a simplified schematic showing concentric primary windings A1 and A2 and concentric secondary windings B1 and B2 for generating the voltages V'1 and V'2.
Figure 4:
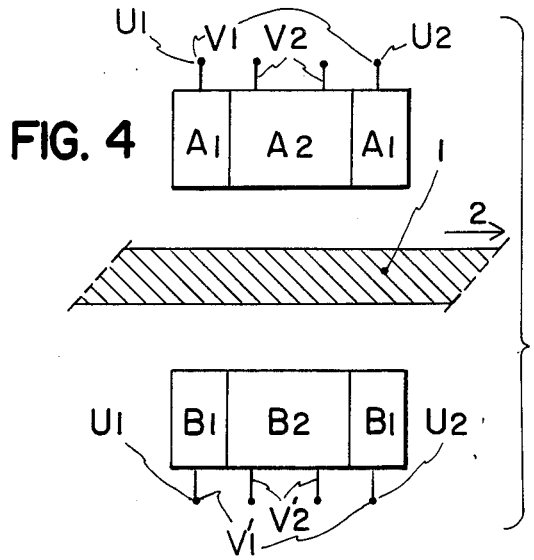
FIG. 4 is a simplified schematic view similar to FIG. 3 showing concentric primary and secondary windings for generating phase displacement voltages V1V'1 and V2V'2.
Figure 5:
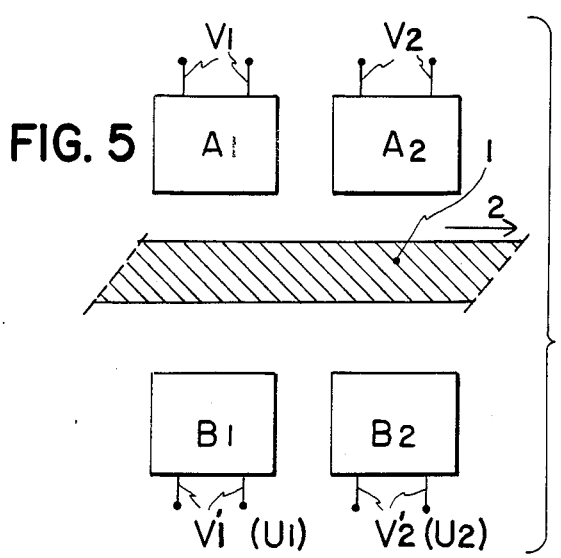
FIG. 5 is a simplified schematic view showing spaced primary windings A1 and A2 and spaced secondary windings B1 and B2 for generating voltages V'1 and V'2.
Figure 6:
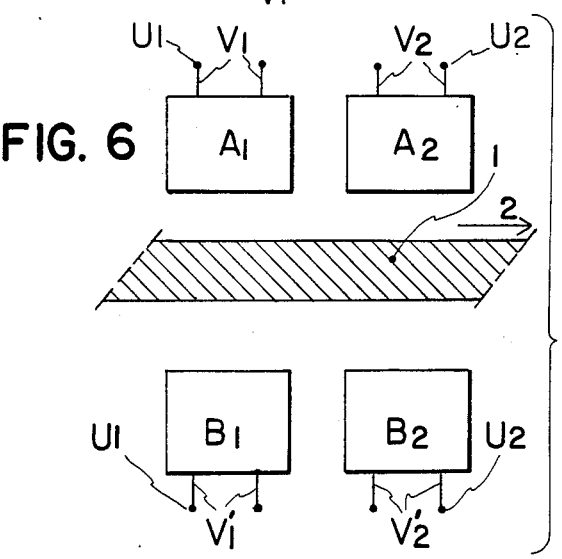
FIG. 6 is a simplified schematic view similar to FIG. 5 showing spaced primary and secondary windngs for generating phase displacement voltage V1V'1 and V2V'2.

FIGS. 3 and 4 relate to the use of concentric primary windings A1 and A2 and secondary windings B1 and B2 with applied voltages V1 and V2 and the induced voltages V'1 and V'2. FIGS. 3 and 4 respectively represent the same differences as FIGS. 1 and 2 as regards the measurement in respect or U1 and U2. FIGS. 5 and 6 relate to the use of two pairs of separate windings A'1-B'1 and A'2-B'2. Applied to each of the pairs are the respective voltages V1 and V2 which respectively develop the induced voltages V'1 and V'2. The differences between FIGS. 5 and 6, as before, concern the two variations in measurement in respect of U1 and U2.

The invention will be better appreciated by reference to the following examples of use thereof:

EXAMPLE 1

Two primary windings were used, being spaced from each other at 3 cm and disposed at a distance of 14 mm above the sheet; applied to those windings were voltages V1 and V2 of 30 volts at a frequency N1 of 30 kHz, for the former in the direction of movement of the sheet, and N2 of 50 kHz, for the latter.

Disposed on the other side of the sheet symmetrically with respect to the primary windings were secondary windings which developed voltages V'1 and V'2 of the order of about ten millivolts, which are used as values of U1 and U2.

Each pair formed by a primary winding and a secondary winding was first calibrated in the following manner:

1. The 0 of the voltage measuring apparatus was set for $\theta = 24°$ C. and $e_0 = 28$ µm.
2. Sheets of different thicknesses are used and the values $U^\theta 1$ and $U^\theta 2$ are measured at constant temperature, thus establishing a curve $U = K/e + C$, on the basis of which the values K1, C1 and K2, C2 are determined.
3. A sheet of constant thickness is used and raised to different temperatures, measuring the values $U^\theta 1$ and $U^\theta 2$ on each occasion. That therefore establishes a curve $U = b + a\theta$ on the basis of which the values a1, b1 and a2, b2 are determined.

The results obtained are as follows:

| Constant temperature | | | | Constant thickness | | | |
| $\theta = 21.2°$ C. | | $\theta = 24°$ C. | | $e_0 = 28$ µm | | | |
| U1 volts | e µm | U2 volts | e µm | U1 volts | $\theta°$ C. | U2 volts | $\theta°$ C. |
| −0.41 | 25.71 | −1.2 | 25.71 | −0.11 | 28.4 | −0.14 | 25.8 |
| −0.22 | 26.41 | −0.76 | 26.41 | −0.16 | 30 | −0.46 | 30.4 |
| 0.52 | 30.28 | 1.15 | 30.28 | −0.22 | 33.1 | −0.73 | 34.1 |
| 0.78 | 31.78 | 1.81 | 31.78 | −0.29 | 36.1 | −1.07 | 38.6 |
| 1.96 | 41.33 | 4.69 | 41.33 | −0.33 | 37.8 | −1.22 | 40.3 |
| 2.01 | 41.78 | 4.80 | 41.67 | −0.38 | 39.4 | −1.53 | 45.0 |
| | | | | −0.40 | 40.4 | −1.66 | 46.7 |
| | | | | −0.49 | 44.2 | −2.08 | 52.8 |
| | | | | −0.56 | 46.9 | −2.37 | 57.0 |
| | | | | −0.63 | 50.2 | −2.59 | 59.7 |
| | | | | −0.75 | 54.8 | −2.58 | 63.2 |
| | | | | −0.86 | 59.7 | | |

From that are deduced the following:

$$a1 = 0.0242 \quad b1 = 0.5811 \quad a2 = 0.0725 \quad b2 = 1.739$$
$$C1 = 5.81 \quad C2 = 14.4$$

and consequently:

$$A1 = (b1 - C1)e_0 = (0.5811 - 5.81) \times 28 = -146.41$$

$$B1 = a1 e_0 = 0.0242 \times 28 = 0.678$$

$$A2 = (b2 - C2)e_0 = (1.739 - 14.4) \times 28 = -354.51$$

$$B2 = a2 e_0 = -0.0725 \times 28 = -2.03$$

The process of the invention was then used for measuring a sheet of aluminium of a known thickness $e = 41.33$ µm at a temperature $\theta = 23°$ C.

The following voltage measurements were taken: U1 = 1.90 volt, U2 = 4.72 volts.

Applying those values and those of the coefficients A1, B1, C1 and A2, B2, C2 established hereinbefore, in the following formulae:

$$e = [A1 B2 - A2 B1]/[(U1 - C1)B2 - (U2 - C2)B1] \text{ and}$$

$$\theta = [A2(U1 - C1) - A1(U2 - C2)]/[B1(U2 - C2) - B2(U1 - C1)]$$

that gives: $e = 41.40$ µm $\theta = 22.8°$ C. or a degree of measuring accuracy of 0.16% in respect of thickness and 0.87% in respect of temperature.

EXAMPLE 2

This Example used a single primary winding A and a single secondary winding B disposed on respective sides of the sheet and at a spacing of 14 mm.

Voltages V1 and V2 of 30 volts at frequencies of 30 kHz and 50 kHz were simultaneously applied to the winding A. The winding B developed an induced voltage V'12, the components V'1 and V'2 of which were separated by means of frequency filters. The phase displacements on the one hand between V1 and V'1 and on the other hand between V2 and V'2, being converted into voltages and then amplified, were used as the values in respect of U1 and U2. The 0 of the voltage measuring apparatus was set for $e_0 = 41.9$ μm and $\theta_0 = 24°$ C., and the calibration operations were effected in accordance with points 2 and 3 of Example 1 above.

The results obtained were as follows:

| Constant temperature | | | | Constant thickness | | | |
|---|---|---|---|---|---|---|---|
| $\theta = 21.2°$ C. | | $\theta = 20.6°$ C. | | $e = 41.9$ μm | | | |
| U1 volts | e μm | U2 volts | e μm | U1 volts | $\theta°$ C. | U2 volts | $\theta°$ C. |
| −4.18 | 25.71 | −7.65 | 25.71 | −0.15 | 27.7 | −0.14 | 25.7 |
| −3.88 | 26.41 | −7.65 | 26.41 | −0.27 | 30.2 | −0.30 | 27.7 |
| −2.48 | 30.28 | −5.04 | 30.28 | −0.31 | 31.9 | −0.61 | 31.3 |
| −2.03 | 31.78 | −4.15 | 31.78 | −0.48 | 37.2 | −0.90 | 35.0 |
| 0.04 | 41.33 | 0.09 | 41.33 | −0.66 | 41.9 | −1.07 | 36.7 |
| | | | | −0.81 | 45.4 | −1.52 | 42.4 |
| 0.13 | 41.67 | 0.22 | 41.67 | −1.03 | 51.0 | −1.96 | 47.8 |
| | | −1.53 | 37.0 | −1.14 | 53.7 | −2.24 | 51.5 |
| | | | | −1.36 | 59.5 | −3.02 | 60.6 |

Deduced therefrom were the following values of the constants:

$$A1 = -257.14 \quad B1 = -1.613 \quad C1 = 7.06$$
$$A2 = -511.9 \quad B2 = -3.47 \quad C2 = 14.20$$

The process according to the invention was then applied to a sheet of aluminium of a known thickness of 28.0 μm and at a temperature of 23° C.

The following voltage measurements were taken:
U1 = −3.45 volts; U2 = −6.94 volts.

By using those values in the formulae in respect of e and $\theta$, that gave:

$e = 28.08$ μm and $\theta = 23.56°$ C., namely a degree of accuracy of 0.3% in respect of thickness and 2.4% in respect of temperature.

It will be possible to appreciate the attraction of the present process which finds application in continuous measurement without the risk of damage due to the measuring instrument, of the thickness and the temperature of sheets of a thickness of between 8 and 2000 μm at a temperature of between 0° and 150° C. and in particular aluminium sheets at the discharge of rolling mills.

What is claimed is:

1. A method for the non-contacting measurement of the thickness (e) and temperature ($\theta$) of a thin metal sheet while in motion during a manufacturing operation comprising:
   generating on the same side of the sheet two separate magnetic fields by applying to at most two primary windings (A1) and (A2) a voltage V1 of a frequency N1 and a voltage V2 of a frequency N2 so as to develop respectively the induced voltages V'1 and V'2 in at most two secondary windings (B1) and (B2) placed on the other side of the sheet and respectively facing (A1) and (A2);
   determining a voltage U1 in volts in the electrical circuit using V1 and V'1 and a voltage U2 in the circuit using V2 and V'2 where U1 and U2 are directly related to V1, V'1 and V2, V'2 respectively;
   establishing the relationship $U = K/e + C$ where K and C are constants which is obtained by measuring the voltage $U^\theta 1$ generated by a field of frequency N1 when it passes through sheets of different thicknesses but at a constant temperature the likewise the voltages $U^\theta 2$ for a frequency N2, and deducing the values of the constants C1 and C2 respectively correspondng to two values of C for the frequencies N1 and N2, it being known that the 0 of the volage measuring apparatus has been regulated to a reference thickness $e_0$ and a temperature $\theta_0$;
   establishing the relationship $U = b + a\theta$ where b and a are constants which is obtained by measuring the voltages $U^\theta 1$ generated by a field of frequency N1 when it passes through sheets of different temperatures but of constant thickness and likewise for the voltages $U^\theta 2$, the zero of the voltage measuring apparatus also being regulated for $e_0$ and $\theta_0$ and deducing the values of the constants a1, a2, b1, b2, whose indices 1 and 2 correspond to the frequencies N1 and N2;
   using the values of said constants a, b and c to determine the values of other constants A1, A2, B1 and B2 from the following equations:

$$A1 = (b1 - C1)e_0 \quad A2 = (b2 - C2)e_0$$
$$B1 = a1e_0 \quad B2 = a2e_0;$$

and
   determining the values of e and $\theta$ by introducing the values of the constants A1, B1, C1, A2, B2, C2 and the values of U1 and U2 observed on the metal sheets to be measured into the following formulae:

$$e = [A1B2 - A2B1]/[(U1 - C1)B2 - (U2 - C2)B1]$$ and $$\theta = [A2(U1-C1) - A1(U2-C2)]/[B1(U2-C2) - B2(U1-C1)].$$

2. A method according to claim 1 characterised in that the voltages U1 and U2 respectively correspond to V'1 and V'2.

3. A method according to claim 1 characterised in that the voltages U1 and U2 respectively correspond to the phase displacement values on the one hand as between V1 and V'1 and on the other hand as between V2 and V'2 after transformation of said values into voltages expressed in volts.

4. A method according to claim 1 characterised by successively applying the voltages V1 and V2 to a single winding (A) in order successively to develop the voltages V'1 and V'2 at the terminals of a single winding (B).

5. A method according to claim 1 characterised by simultaneously applying the voltages V1 and V2 to a single winding (A) to develop at the terminals of a single winding (B) an induced voltage V'12 which is separated into its components V'1 and V'2 by means of frequency filters.

6. A method according to claim 1 characterised by applying the voltages V1 and V2 to two concentric windings (A1) and (A2) and developing the voltages at the terminals of two concentric windings (B1) and (B2) which are separated into their components V'1 and V'2 by means of frequency filters.

7. A method according to claim 1 characterised by applying the voltages V1 and V2 to two concentric windings (A1) and (A2) and developing a voltage at the terminals of a single winding (B), which is separated into its components V'1 and V'2 by means of frequency filters.

8. A method according to claim 1 characterised by applying the voltages V1 and V2 to two windings A'1 and A'2 which are separate from each other and developing the voltages V'1 and V'2 at the terminals of two windings (B'1) and (B'2) which are separate from each other.

9. A method according to claim 1 characterised in that the frequencies N1 and N2 are between $1.10^2$ and $1.10^5$ Hertz.

10. A method according to claim 1 characterised in that it is applied to metal sheets of a thickness of between 8 and 2000 μm.

* * * * *